United States Patent [19]

Brummond et al.

[11] 4,412,820
[45] Nov. 1, 1983

[54] ORTHODONTIC TENSION-APPLYING APPARATUS

[75] Inventors: Gerald G. Brummond, Canby; Paul E. Klein, Lake Oswego; Roland M. Anderson, Wilsonville, all of Oreg.

[73] Assignee: Modcom, Inc., Canby, Oreg.

[21] Appl. No.: 373,359

[22] Filed: Apr. 30, 1982

[51] Int. Cl.³ .............................................. A61C 7/00
[52] U.S. Cl. ..................................................... 433/18
[58] Field of Search ............................ 433/11, 18, 22; 206/820

[56] References Cited

U.S. PATENT DOCUMENTS 2,928,100  3/1960  Gagnon .............................. 206/820
4,038,753  8/1977  Klein ..................................... 433/18

Primary Examiner—Robert Peshock
Attorney, Agent, or Firm—Kolisch, Hartwell & Dickinson

[57] ABSTRACT

Elastomeric, orthodontic, tension-applying apparatus, and a method for molding the same to yield a device characterized by highly uniform eleasticity properties. In the final molded product, plural endless loops are interconnected, in a chain-like fashion, by integral tensioning structure, with each loop joined to the side of an elongated carrier prong through an individual isthmus. These isthmuses result, during the molding process, from individual flow-gating which is provided for each loop, and such gating is key to ultimate elasticity uniformity.

2 Claims, 5 Drawing Figures

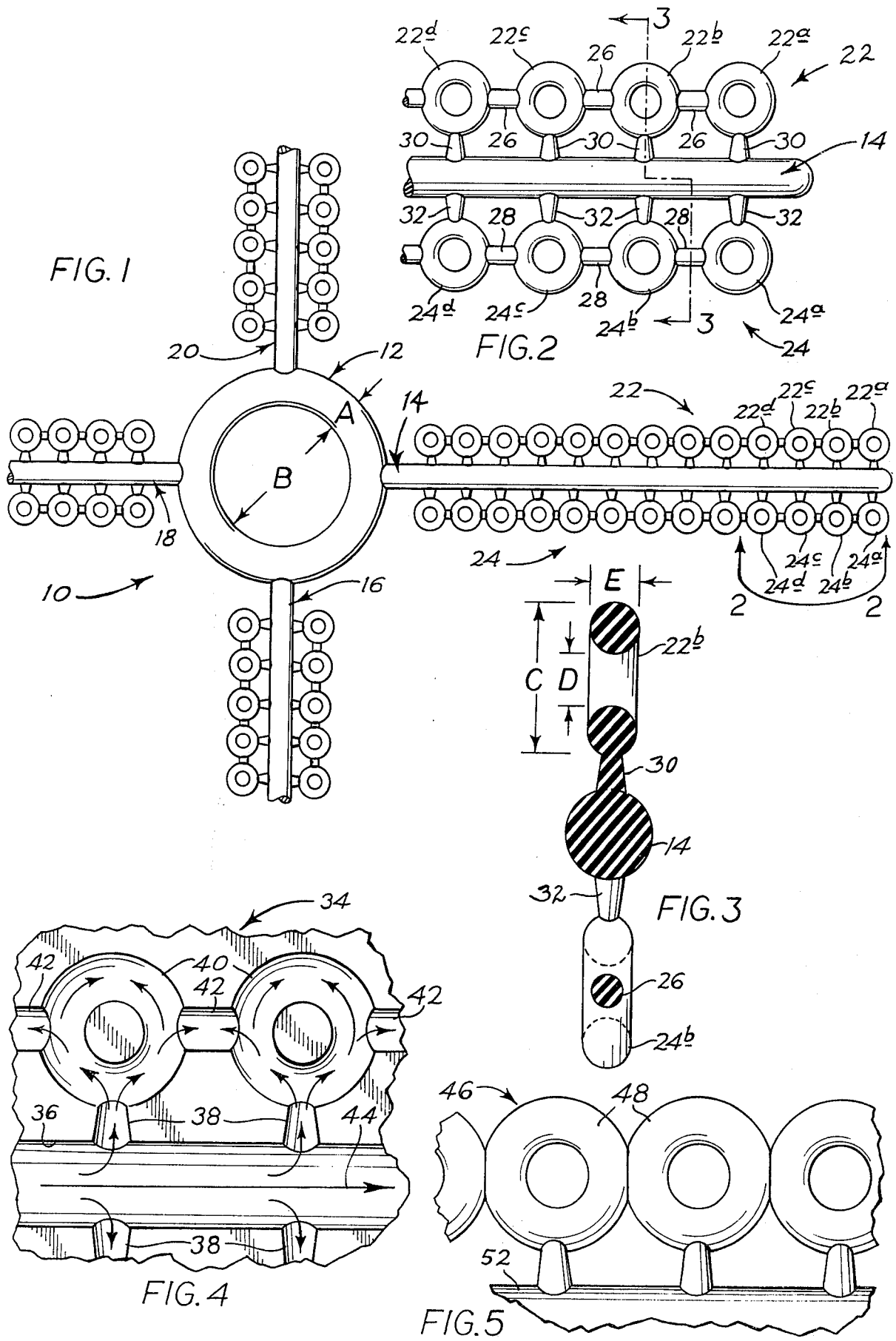

ORTHODONTIC TENSION-APPLYING APPARATUS

BACKGROUND AND SUMMARY OF THE INVENTION

The present invention relates to a molded elastomeric orthodontic product, and to a method of forming the same. More paraticularly, it relates to a chain-like tension-applying product (and related method), which is characterized by a high degree of elasticity uniformity.

For a number of years, chain-like orthodontic tension-applying elastomers have been available. In many cases these have been molded products in which plural O-ring-like endless loops are interconnected to form a string which may be cut to different lengths depending upon installation requirements.

A problem which has surfaced in the past with molded chains of the type described, is that the chains exhibit nonuniform elasticity along their lengths. In other words, there are certain regions which have less tensile strength than others, and when these regions are "worked" in an installation, they often fail, or at least weaken, far earlier than is normally expected.

With this situation in mind, a general object of the present invention is to provide a unique chain-like tension-applying product or apparatus, and a method for molding the same to yield a final product which is characterized by highly uniform elasticity properties which obviate problems found in prior molded chains.

According to the invention, in the final molded product, plural endless loops, or chain-loop articles, are interconnected, in a chain-like fashion (as is found in prior art chains), by integral tensioning structure, with each loop joined to one side of an elongated carrier prong through an individual flow-gated isthmus. These individual isthmuses associated with the prongs, during the molding process, result from individual flow-gating which is provided for each loop in the mold, and such individual gating is key to ultimate elasticity uniformity. Such individual flow-gating utilized by the invention assures the maximum uniformity of flow in the mold regions shaped to form the final chain product.

Flow-gating in prior known molds has been provided at relatively large intervals along a chain encompassing more than one loop in the chain. Individual flow-gating, as proposed by the method of the invention, uses, ultimately, only a slightly greater amount of mold material in the final product (as compared with current molded chain products), yet produces a final chain with elasticity characteristics which are significantly more uniform.

These and other objects and advantages which are attained by the invention will become more fully apparent as the description which now follows is read in conjunction with the accompanying drawings.

DESCRIPTION OF THE DRAWINGS

FIG. 1 is a fragmentary plan view of a molded orthodontic unit formed in accordance with teachings of the present invention.

FIG. 2 is an enlarged fragmentary view generally of that portion of the unit shown in FIG. 1 which is embraced by the double-arrowed curved line 2—2 in FIG. 1.

FIG. 3 is a cross-sectional view, on a larger scale than FIG. 2, taken generally along the stepped cross section line 3—3 in FIG. 2.

FIG. 4 is a fragmentary plan detail of one side of a mold die used in the formation of the unit shown in FIG. 1, illustrating liquid elastomer flow during a molding procedure.

FIG. 5 is a fragmentary detail, on about the same scale as FIG. 3, showing a modified form of molded chain device differing from those shown in FIGS. 1, 2 and 3 in the nature of tensile interconnections provided between adjacent loops in the chain.

DETAILED DESCRIPTION OF THE INVENTION

Turning now to the drawings, and referring first to FIG. 1, indicated generally at 10 is a molded orthodontic unit which includes, as will be explained, tension-applying elastomeric chain devices constructed and formed in accordance with the present invention. Unit 10 herein is configured with a central supporting ring 12, from which radiate four elongated prongs 14, 16, 18, 20. The ring and prongs are referred to herein collectively as a dispensing unit. A material found to be extremely satisfactory for molding of unit 10 comprises a well-known, conventional, elastomeric, thermoset-thermoplastic, polyester-based, isocyanate-terminated, urethane resin. This kind of material, used for a number of years with orthodontic elastomer appliances, has proven to function as a tough, elastomeric, mouth-fluid-resistant material, which is capable of enduring long periods of use in the mouth without any appreciable deterioration, or loss of tension-applying capability.

Considering now FIGS. 2 and 3 along with FIG. 1, distributed along two opposite sides of each prong are tension-applying chains, like the two shown generally at 22, 24 on upper and lower sides, respectively, of prong 14 in FIGS. 1 and 2. Each of chains 22, 24 includes a plurality of endless loops, such as the four outer loops or chain-loop articles, 22$a$, 22$b$, 22$c$, 22$d$ shown in chain 22, and the four outer loops 24$a$, 24$b$, 24$c$, 24$d$ shown in chain 24. These loops, in the embodiment of the invention now being described, have circular cross sections, as can be seen for loop 22$b$ in FIG. 3. Each two adjacent loops are interconnected by an integral strand, or tensioning structure, such as the strands shown at 26 between the identified loops in chain 22, and the strands shown at 28 between the identified loops in chain 24.

Joining each loop in chain 22 directly to prong 14 is what is referred to herein as a flow-gated isthmus, such as those shown at 30. Similarly, joining each loop in chain 24 to prong 14 is a similar isthmus, such as those shown at 32. These isthmuses, which are provided individually for each loop in each chain, and which are formed, as will be explained, during the molding procedure for unit 10, are key to the resulting performance characteristic of the chains in the unit, with respect to uniformity of tensile strength throughout the entire lengths of the chains.

While units, like unit 10, having differing dimensions may be formed to suit different final applications, in unit 10, the prongs have cross-sectional diameters of about 0.313-inches, and the ring (12) supporting the prongs has a cross-sectional diameter, shown at A in FIG. 1, of about 0.375-inches, and an internal ring diameter, shown at B in FIG. 1, of about 0.625-inches. Each of the chains in unit 10 is formed with twelve strand-interconnected loops, with each loop having an outer diameter, shown at C in FIG. 3, of about 0.12-inches, an inner diameter, shown at D in FIG. 3, of about 0.06-inches, and a cross-sectional diameter, shown at E in FIG. 3, of about 0.03-inches. The strands between each loop in each chain have lengths of about 0.03-inches, and cross-sectional diameters of substantially the same dimension. The isthmuses take the form, generally speaking, of truncated cones, with large-diameter bases, where they join with prong 14, having diameters of about 0.025-inches, and small-diameter bases, where they join with a loop, having diameters of about 0.015-inches. Each isthmus is about 0.03-inches long.

FIG. 4 shows at 34 a fragmentary plan detail of the "working" face of a typical molding die used in the formation of units like unit 10. Visible in this die face is an elongated semi-cylindrical channel 36, which functions for the formation of a prong like prong 14. Extending from opposite sides of channel 36 are truncated semi-conical passages 38, which are used in the formation of flow-gated isthmuses like isthmuses 30, 32. At the other end of each passage is a generally circular, and semi-cylindrical in cross section, trough 40 used in the formation of loops, such as the loops indicated in chains 22, 24. Extending between each trough 40 is a semi-cylindrical channel 42 used in the formation of the interconnecting strands, such as those indicated earlier at 26, 28.

Arrows in FIG. 4 generally indicate the manner in which liquid resin flows in the mold during a molding operation. Regarding the die portion shown in FIG. 4, what might be thought of as the main flow of resin occurs as indicated by arrow 44 along the length of channel 36. This flow ultimately forms a prong, like prong 14. From channel 36, resin diverts outwardly in streams through each of passages 38 into troughs 40 where it splits into two forks. In these two forks, resin flows around the trough, and meets with itself, so-to-speak, at the opposite side ultimately to create the endless loops. From opposite sides of the troughs, resin flows outwardly into the ends of channels 42 to establish the connective stands between the loops.

The importance of the resin-flow pattern indicated in FIG. 4 is that such flow results in a final per-article molded chain product which is uniform, vis-a-vis its density, along the entirety of its length. This uniformity results from a key feature relating to the fact that passages 38 provide for resin flow-gating for each loop article in a chain As a consequence, these passages assure uniformly dense filling of all molded cavities provided for making up a chain, and lead to a finally formed product which has highly uniform elasticity characteristics.

In the hands of an orthodontist, a final product such as unit 10 is then used in a conventional manner. Through any suitable cutting device, the orthodontist cuts off precisely the length of chain, i.e., numbers of loops, which he intends to use, and also cuts these loops away from the associated isthmuses. A cut chain length is then installed in the normal manner.

Turning attention for a moment to a modification shown in FIG. 5, there are some applications where it is desirable to use chains having loops which are tangentially interconnected, rather than being interconnected through strands. In this figure, a fragment of such a chain is shown generally at 46. Chain 46 has loops 48 which are tangentially integral, as shown, with each loop individually connected through an isthmus 50 (which is like the isthmuses previously described) to a side of a prong shown fragmentarily at 52. Formation of a chain device like that shown in FIG. 5 is accomplished with a per-article flow-gated mold which functions in substantially the same manner described in connection with FIG. 4.

It should thus be appreciated how the method of the present invention, and the product resulting therefrom, obviate the problems described earlier that have characterized the tension-applying reliability problem of prior known molded orthodontic chains.

While preferred embodiments of, and a method of practicing, the invention have been described herein, it is appreciated that variations and modifications may be made without departing from the spirit of the invention.

It is claimed and desired to secure by Letters Patent:

1. Interconnected, plural-article, molded, unitary, elastomeric orthodontic apparatus characterized by uniform elasticity resulting from per-article, controlled flow-gating during molding, said apparatus comprising
   an elongated dispenser unit,
   a plurality of endless chain-loop articles distributed along said unit, with each pair of adjacent loop articles being operatively interconnected by an integral tensioning structure, and
   for each article, a flow-gated isthmus severably connecting the article to the unit.

2. Interconnected, plural-article, molded, unitary, elastomeric orthodontic apparatus characterized by uniform elasticity, resulting from per-article, controlled flow-gating during molding, said apparatus comprising
   a device including a central ring and plural elongated prongs which project outwardly from sides of said ring,
   associated with each prong, a plurality of endless chain-loop articles distributed along the prong, with each pair of adjacent articles being operatively interconnected by an integral tensioning structure which is severable to disconnect such adjacent articles, and
   for each article associated with each prong, a flow-gated isthmus severably connecting the loop article and the prong.

* * * * *